United States Patent [19]

Perrot

[11] Patent Number: 4,938,933
[45] Date of Patent: Jul. 3, 1990

[54] MEDICAL AND SURGICAL INSTRUMENT CLEANING AND DISINFECTING DEVICE

[76] Inventor: Jean J. M. V. A. Perrot, 304, rue Garibaldi, Lyon 7eme, Rhône, France

[21] Appl. No.: 178,339

[22] Filed: Apr. 6, 1988

[30] Foreign Application Priority Data

Apr. 13, 1987 [FR] France .................. 87 05564

[51] Int. Cl.⁵ .................. B8B 5/02; A61L 2/00
[52] U.S. Cl. .................. 422/292; 422/293; 422/306; 422/108; 134/56 R; 134/100; 134/199
[58] Field of Search .............. 422/3, 28, 31, 292, 422/293, 119, 306, 108, 300; 134/56 R, 100, 199; 55/443

[56] References Cited

U.S. PATENT DOCUMENTS

| | | | |
|---|---|---|---|
| 3,254,475 | 6/1966 | Farr et al. | 55/443 |
| 3,699,984 | 10/1972 | Davis | 134/199 |
| 3,757,806 | 9/1973 | Bhaskar et al. | 134/199 |
| 3,918,987 | 11/1975 | Kepfer | 134/199 |
| 4,263,258 | 4/1981 | Kalasek | 422/26 |
| 4,452,264 | 6/1984 | Kreisel et al. | 134/199 |
| 4,552,163 | 11/1985 | Biancalana et al. | 134/199 |
| 4,670,010 | 6/1987 | Dragone | 422/292 |
| 4,688,585 | 8/1987 | Vetter | 134/56 R |
| 4,817,651 | 4/1989 | Crisp et al. | 134/199 |

Primary Examiner—Barry S. Richman
Assistant Examiner—Gregory R. Muir
Attorney, Agent, or Firm—Browdy and Neimark

[57] ABSTRACT

A medical and surgical instrument cleaning and disinfecting device consisting of a tubular body whose one end is open and whose other end is equipped with a liquid collection tank is shown. The detector senses the presence of an instrument inside of the tubular body and controls pressurized diffusion of a nebulized disinfection product which is sprayed on the instrument. A suction device pulls disinfection spray towards a reservoir.

12 Claims, 2 Drawing Sheets

MEDICAL AND SURGICAL INSTRUMENT CLEANING AND DISINFECTING DEVICE

BACKGROUND OF THE INVENTION

1. Field of the Invention

This invention relates to a medical and surgical instrument cleaning and disinfecting device.

2. The Prior Art

Practitioners, whether surgeons, dental surgeons or physicians, use instruments that cannot always be perfectly sterilized or disinfected between two successive operations.

This is particularly the case of handpieces, counterangles, ultrasound apparatus and three-way vaporizers constantly used by dental surgeons.

Actually, since these instruments are solidly connected to the care console, it is not possible to remove them to perform a complete cleaning between two successive operations.

These instruments can undergo considerable contamination from microbes or viruses contained in gangrenous teeth, on the outside of teeth with dental plaque, in the saliva or blood. These microbes or viruses therefore can be sprayed, under the action of the turbine in the patient's mouth, onto the basic instrument itself, onto the mirror, tongue retractor or also on the probe the practitioner uses to protect the integument from untimely drilling cuts. Besides the risk of contamination of one patient by another, there are considerable contamination risks of medical personnel.

These contaminations have particularly serious consequences in the case of diseases that are difficult to treat such as hepatitis B or for which a treatment is not yet available such as AIDS.

SUMMARY OF THE INVENTION

This invention aims at providing a device making it possible to clean and disinfect an instrument simply and quickly, while avoiding any risk of transmission of microbes or viruses.

For this purpose, the device to which it relates comprises in combination, a tubular body whose one end is open and whose other end is equipped with a liquid collection tank, means for detecting the presence of an instrument inside the tubular body inside the tubular body, located near the open end of the latter, and means for pressurized diffusion of a nebulized disinfection product, operated by detection means when the detection means detect the presence of an instrument.

The practitioner having in hand an instrument to be cleaned, it suffices to introduce it into the tubular body of the device, this instrument receiving, after detection of its presence, a spraying of disinfectant fluid. Considering the pressure of the diffused fluid, this fluid assures not only disinfection of the instrument but also a cleaning of it, the contamination in liquid or particle form being driven off under the effect of the pressure of the fluid.

This equipment is interesting because of the automatic nature of its control, which enables a practitioner, not having a free hand, to clean and disinfect an instrument at the end of an operation and/or before an operation.

Advantageously, the inside wall of the tubular body is inclined downward from its open end to its end equipped with the tank. This inclination assures an evacuation by gravity of the condensed disinfection liquid and of the contamination toward the collection tank.

According to another characteristic of the invention, the means for diffusion of the disinfection fluid consist of a plurality of injectors, regularly distributed on the periphery of the body and coming out inside it, each injector comprising a mixing chamber in which air is brought to the center and the disinfecting liquid is brought in peripherally.

The pressurized air can be supplied by the compressed air network equipping every operating room and every dental surgeon's office. The various injectors are also fed disinfecting liquid from a liquid tank located close to the device. The number of injectors and their arrangement are a function of the angle of diffusion of each of them, the essential point being to assure a projection of fluid over the entire periphery of the instrument.

According to an embodiment, the device body comprises a first tubular part, located on the side of the open end, containing means for presence detection and product diffusion and a second tubular part which, removably mounted on the first part, is equipped in a removable way, at its other end, with the collection tank.

Although various solutions can be envisaged, such as a single-piece body, which may or may not have an integral tank, the construction without the integral tank is advantageous since it makes it possible to assemble, in a first tubular part, the various elements necessary for operation of the device and to have two other very simple structural parts. It is also possible for the practitioner to remove the tank during the day to empty it and, at the end of the day, to remove the tank, on the one hand, and the second tubular part, on the other hand, to sterilize them.

To promote the flow of the condensed liquid and the contamination inside the tubular element, and to limit contamination of the latter, the injectors and presence detector elements are not located on the low generatrix of the tubular body.

According to an embodiment, the elements for detection of the presence of the instrument are located upstream from the cleaning and disinfecting liquid diffusion device in the direction of the introduction of an instrument into the tubular body.

According to another possibility, this device comprises, on its front face, elements for detection of the presence of the practitioner's hand holding the instrument to be cleaned.

According to an advantageous embodiment, the tubular body is equipped with a suction device on the side of its end comprising a liquid collection tank. Further, between the product diffusion means and the suction connection, the tubular body is equipped with a system of baffles intended to promote condensation of the nebulized product. This arrangement makes it possible to keep the nebulized liquid from escaping from the tubular body, which would be disagreeable and even dangerous for the practitioner. The suction device can be solid with the device or be at a distance from it and connected to it by a pipe.

Advantageously, and to keep from wetting the instruments excessively, the disinfection liquid used is not explosive, evaporates rapidly, and has bactericidal, fungicidal and virucidal action. With such a liquid, cleaning and disinfecting are performed in a few seconds under a jet of fluid at a pressure less than five bars, for example, on the order of two to four bars.

BRIEF DESCRIPTION OF THE DRAWINGS

In any case, the invention will be better understood from the following description with reference to the accompanying diagrammatic drawings representing, by way of nonlimiting example, an embodiment of this device, in which.

DETAILED DESCRIPTION OF THE PREFERRED EMBODIMENTS

Figure 1:
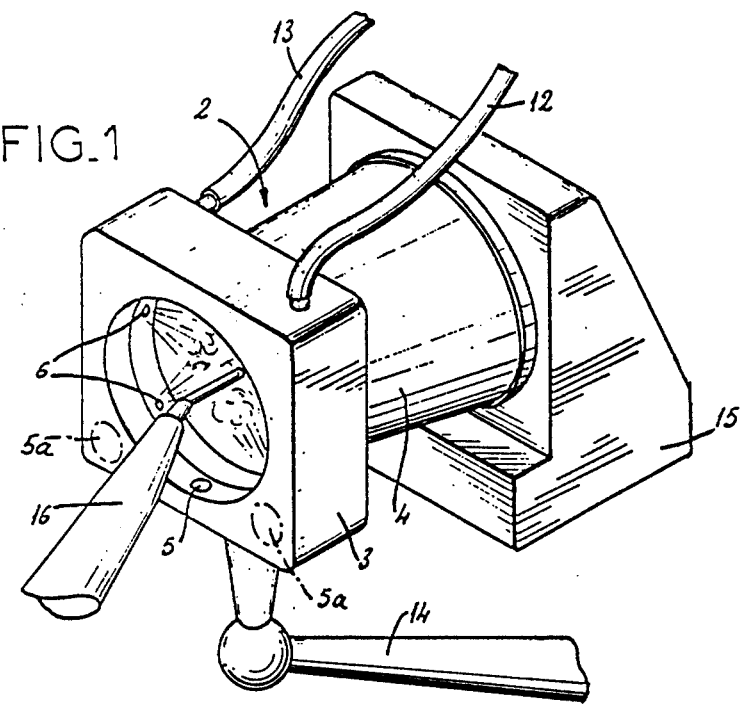
FIG. 1 is a perspective view of the device according to the present invention.
Figure 2:
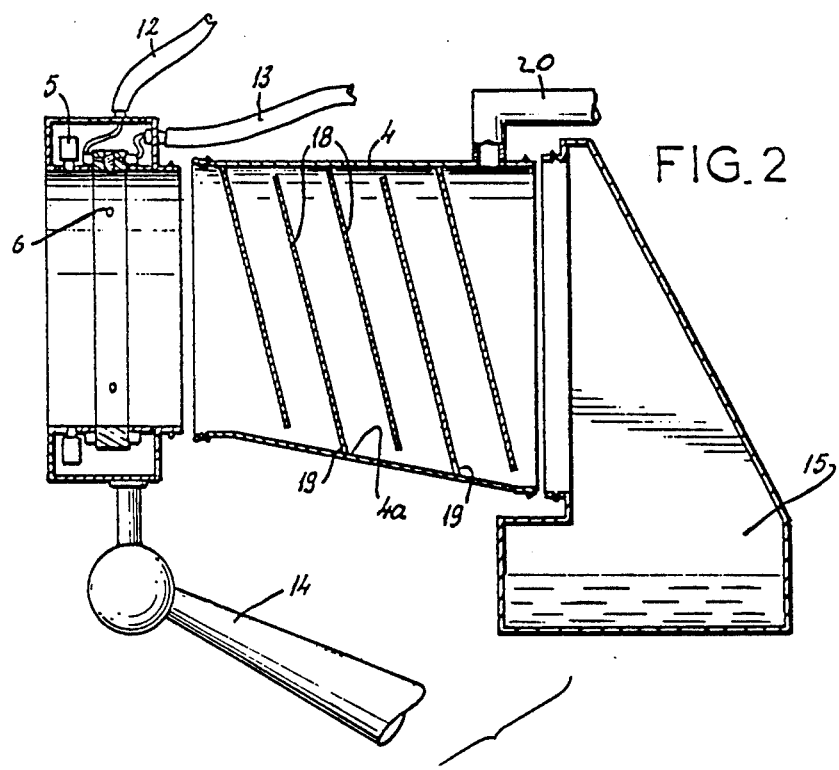
FIG. 2 is a view in longitudinal section according to the present invention.
Figure 3:
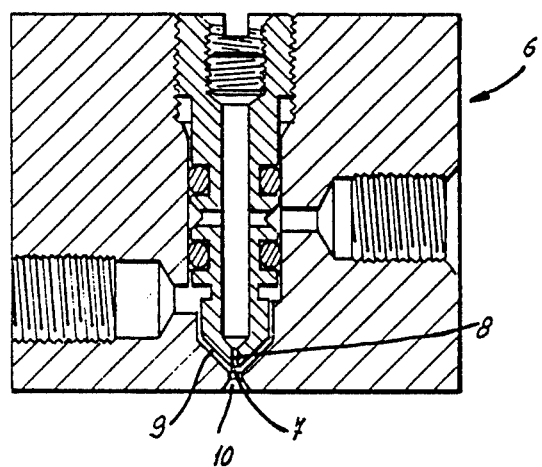
FIG. 3 is a view in section and on an enlarged scale of an injector according to the present invention.

The device, represented in the drawings, comprises a tubular body designated by general reference 2 comprising a front part 3 and a back part 4. The front part, in the shape of a crown, is equipped with a device for detection of the presence of an instrument, consisting, in the embodiment represented in the drawing, of a photoelectric or electromagnetic cell 5.

A variant consists in providing presence detectors 5a located on the front face of the body, which detect the nearness of the hand of the practitioner holding the instrument.

Near photoelectric cell 5 are placed a plurality of injectors 6 regularly distributed on the periphery of element 3 and coming out in its central cavity.

Each injector 6 comprises a chamber 7 for mixing air and disinfectant liquid in which air is brought by a central orifice 8 and the disinfecting liquid is brought by a peripheral orifice 9. The pressurized air aspirates the nebulized liquid, the mixture coming out in the central part of the body of the device by an orifice 10.

In the embodiment represented in the drawings, each injector is placed radially, although it is possible to envisage an inclined position of the injectors. The air is brought to each injector by a duct 12 connected to a pressurized air network of the installation, while the disinfecting liquid is brought by a pipe 13 from a tank (not shown).

In the embodiment represented in the drawing, front part 3 of the body of the device is solid with an arm 14 allowing it to be fastened to a care console. To part 3 is fastened, for example by locking, tubular part 4 whose bottom 4a is inclined downward and from the end where it is fastened to part 3 toward its other end. To this end can be fastened, by locking, a tank 15 used to collect the condensed cleaning fluid and contamination collected during cleaning.

It should be noted that, for ease in maintenance of the device, injectors 6 and presence detection devices 5 do not project inside it.

In practice, it suffices for the practitioner, desiring to clean and disinfect an instrument, such as handpiece 16 represented in FIG. 1, to introduce this instrument inside the body of the device. As soon as the presence of this instrument is detected by cell 5, pressurized cleaning and disinfecting fluid is diffused by injectors 6 on the entire periphery of the instrument for several seconds.

During this operation, the contamination is evacuated from the instrument and it is disinfected by the fluid. The condensed fluid and contamination are evacuated to tank 15 by gravity along inclined lower wall 4a of the tubular body.

According to an advantageous embodiment, tubular body 4 is equipped, close to its back end, with a suction connection 20, connected to the suction device (not shown in the drawing). Further, tubular body 4 comprises a series of baffles 18, nevertheless making a passage 19 in the lower part for flow of the liquid, these baffles 18 aiming at promoting the condensation of the nebulized liquid and as much as possible keeping the liquid particles from being brought to the suction device.

As comes out from the above, the invention makes a great improvement in the existing technique by providing a device of simple design making it possible rapidly and efficiently to clean and disinfect medical or surgical instruments, thus avoiding risks of contamination by these instruments.

The foregoing description of the specific embodiments will so fully reveal the general nature of the invention that others can, by applying current knowledge, readily modify and/or adapt for various applications such specific embodiments without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation.

I claim:

1. A device for cleaning and disinfecting medical and surgical instruments with a neublized disinfection fluid, comprising in combination:

a horizontally disposed tubular body having a first open end and a second end connected to a liquid collection tank;

said tubular body having a condensation means for promotion of condensation of nebulized disinfection fluid;

a suction means connected to said device for drawing air and nebulized disinfection fluid through said condensation means such that condensation of the fluid occurs;

detecting means for detecting the presence of an instrument inside said tubular body, said detecting means located near the open end of said tubular body;

diffusion means for pressurized diffusion of nebulized disinfection fluid, responsive to detection by said detecting means; and wherein said tubular body comprises an inside wall inclined downward from the open end to the second end connected to the tank.

2. The device according to claim 1, wherein said diffusion means consists of a plurality of injectors, regularly distributed on an inside periphery of said tubular body, each injector comprising a mixing chamber in which air is brought to a center portion thereof and the disinfecting product is brought in peripherally.

3. The device according to claim 1, wherein said tubular body further comprises:

a first tubular part, located at the open end of said tubular body, containing said detection means and said diffusion means; and a second tubular part located between said first tubular part and said collection tank, having one end removably mounted on said first tubular part, and having said collection tank which is removably mounted on said second end.

4. The device according to claim 2, wherein said injectors and said detecting means are not located on the lower portion of said tubular body.

5. The device according to claim 4, wherein said detecting means are located, on said tubular body, upstream from said diffusion means in the direction of the introduction of an instrument into the tubular body.

6. The device according to claim 1, further comprising means for detection of the presence of a practitioner's hand holding an instrument to be cleaned on a front face of said tubular body.

7. The device according to claim 1, wherein said tubular body is adapted to be connected to said liquid collection tank and said suction means is connected near said tubular body second end.

8. The device according to claim 7, wherein said condensation means has a system of baffles.

9. A device for cleaning and disinfecting medical and surgical instruments with a nebulized disinfection fluid comprising in combination:
  a tubular body having first and second openings, and having said first opening higher than said second opening;
  wherein said tubular body has its lowest surface inclined downward to said second opening with respect to a horizontal plane;
  said tubular body having a condensation means for promotion of condensation of nebulized disinfection fluid;
  a reservoir connected to said tubular body second opening;
  a suction means connected to said device for drawing air and nebulized disinfection fluid through said condensation means such that condensation of the fluid occurs;
  means for detecting the presence of an instrument in said tubular body; and
  means for spraying disinfection fluid responsive to said means for detecting wherein said means for spraying is operative when said means for detecting detects a medical instrument.

10. The device in accordance with claim 9 wherein said inclination of said tubular body lower surface provides for gravity drainage of condensed fluid particles.

11. The device in accordance with claim 9 wherein said suction means prevents escape of any nebulized disinfecting fluid.

12. The device of claim 9 wherein said condensation means comprises a series of baffles which allow condensation, and which do not contact the lowermost portion of said body in order to allow flow of condensate along the lowermost portion of the tubular body.

* * * * *